United States Patent
Buske (10) Patent No.: US 8,920,610 B2
(45) Date of Patent: Dec. 30, 2014

(54) METHOD AND APPARATUS FOR DETECTING IONISABLE GASES IN PARTICULAR ORGANIC MOLECULES, PREFERABLY HYDROCARBONS

(75) Inventor: Christian Buske, Bielefeld (DE)

(73) Assignee: PlasmaTreat GmbH, Steinhagen (DE)

( * ) Notice: Subject to any disclaimer, the term of this patent is extended or adjusted under 35 U.S.C. 154(b) by 95 days.

(21) Appl. No.: 13/145,894

(22) PCT Filed: Jan. 22, 2010

(86) PCT No.: PCT/EP2010/050713
§ 371 (c)(1),
(2), (4) Date: Nov. 15, 2011

(87) PCT Pub. No.: WO2010/084166
PCT Pub. Date: Jul. 29, 2010

(65) Prior Publication Data
US 2012/0067716 A1    Mar. 22, 2012

(30) Foreign Application Priority Data
Jan. 23, 2009  (DE) .......................... 10 2009 006 016

(51) Int. Cl.
  *H05F 3/00*   (2006.01)
  *G01N 27/70*  (2006.01)
  *G01N 33/00*  (2006.01)

(52) U.S. Cl.
  CPC ............ *G01N 27/70* (2013.01); *G01N 33/0047* (2013.01)
  USPC .......................................... 204/164; 422/119

(58) Field of Classification Search
  CPC ........................... G01N 27/70; G01N 33/0047
  USPC .......................................... 204/164; 422/119
  See application file for complete search history.

(56) References Cited

U.S. PATENT DOCUMENTS

| | | | |
|---|---|---|---|
| 4,259,573 A | 3/1981 | Prober et al. | |
| 2006/0043279 A1 | 3/2006 | Kudryavtsev et al. | |
| 2006/0203239 A1* | 9/2006 | Powell et al. | 356/316 |
| 2006/0279297 A1 | 12/2006 | Nystrom et al. | |
| 2007/0114389 A1* | 5/2007 | Karpetsky et al. | 250/288 |
| 2008/0280065 A1* | 11/2008 | Fornsel et al. | 427/569 |
| 2009/0120073 A1* | 5/2009 | Fujita et al. | 60/295 |
| 2009/0165439 A1* | 7/2009 | Hoshi et al. | 60/275 |
| 2010/0021340 A1* | 1/2010 | Buske et al. | 422/28 |

FOREIGN PATENT DOCUMENTS

| | | | |
|---|---|---|---|
| DE | 102005018926 A1 | 2/2006 | |
| DE | 202007018327 U1 | 11/2008 | |
| EP | 0792091 A1 | 8/1997 | |
| EP | 1279955 A1 | 1/2003 | |
| EP | 1557667 A1 | 7/2005 | |
| WO | WO 2007/071720 | * | 6/2007 |

* cited by examiner

Primary Examiner — Xiuyu Tai
(74) Attorney, Agent, or Firm — The Webb Law Firm (57) ABSTRACT

The invention relates to a method for detecting gases that can be ionized wherein an atmospheric plasma jet is produced, wherein a gas mixture is brought into interaction with the plasma jet, and wherein an electrical quantity is measured as a measure of the concentration of the gas in the gas mixture. The invention further relates to a device for detecting gases that can be ionized, including a gas inlet, means for ionizing a gas, a voltage source, two electrodes, and means for determining an amperage, wherein the two electrodes are connected to the voltage source, wherein the means for determining an amperage are connected to the electrodes in such a way that the magnitude of the current flowing between the electrodes can be measured, and wherein a plasma nozzle is provided to produce an atmospheric plasma jet.

8 Claims, 7 Drawing Sheets

METHOD AND APPARATUS FOR DETECTING IONISABLE GASES IN PARTICULAR ORGANIC MOLECULES, PREFERABLY HYDROCARBONS

BACKGROUND OF THE INVENTION

1. Field of the Invention

The invention relates to a method for detecting ionisable gases, in particular organic molecules, preferably hydrocarbons. The invention also relates to an apparatus for detecting ionisable gases, includins a gas inlet, means for ionising an ionisable gas, including a voltage source, two electrodes and means for determining a current strength, the two electrodes being connected to the voltage source and the means for determining a current strength being connected to the electrodes such that the strength of the current flowing between the electrodes can be measured.

2. Description of Related Art

In order to detect organic molecules, for example hydrocarbons in a gas mixture, the flame ionisation detection method is frequently used. In such a method, the gas mixture to be examined is introduced into a flame, in particular into an oxyhydrogen flame. In this flame, the ionisable components of the gas mixture, i.e. in particular organic molecules, are ionised by the thermal energy. The free electrons and ions generated in this way, for example $CHO^+$, will then move according to their charge to respectively one of two electrodes provided, between which a voltage is applied. The current flowing between the electrodes in this way is a measure for the proportion of the ionisable gas, i.e. the concentration of the organic molecules, in the overall gas mixture.

The flame ionisation detection method has the disadvantage that hydrogen and oxygen have to be provided in order to generate the flame. Further, the environment of the burner is intensely heated by the flame. A further disadvantage is that part of the organic molecules is oxidised by the flame. These will then no longer contribute to the current flowing between the electrodes and will therefore not be detected. Therefore, this method is inaccurate.

The concentration of organic molecules in a gas mixture has to be determined, inter alia, in the case of exhaust gases. Thus, for example in the case of exhaust systems, legal requirements in respect of maximum concentrations of certain organic substances have to be complied with. In order to meet such standards, controlled exhaust gas purification systems are often used in the prior art. The measured variable of the concentration of the organic molecules in exhaust gas, which variable is required for controlling, is obtained here, for example, by means of a flame ionisation detector. However, these have the disadvantage that a combustible gas such as for example oxyhydrogen gas is required for the operation of these detectors. Depending on the position of the detector in the exhaust system, however, it is complex, dangerous or even impossible to ensure a supply with this combustible gas.

Determining the concentration of organic molecules in a gas mixture is also required in the general area of gas analytics, for example when a process gas is to be analysed. The disadvantage of the use of flame ionisation detectors here is that the process gas is contaminated by any incompletely burnt proportions of the combustible gas used to feed the flame or by combustion products. This may have a negative effect on the process steps following the analysis.

SUMMARY OF THE INVENTION

The present invention is therefore based on the technical object of providing a method and an apparatus for detecting ionisable gases, in particular organic molecules, preferably hydrocarbons, which at least partially avoids the above-mentioned disadvantages.

According to the invention, this object is achieved by means of a method wherein an atmospheric plasma jet is generated, a gas mixture containing the ionisable gas is made to interact with the plasma jet and an electrical variable is measured so as to be used as a measure for the concentration of the ionisable gas in the gas mixture.

Due to the fact that the gas mixture is made to interact with an atmospheric plasma jet, the ionisable gas contained therein is at least partially ionised by the plasma jet. The free electrons and ions which develop as a result constitute movable charge carriers, through which an electric current is generated that is measured so as to be used as a measure of the concentration of the ionisable gas in the gas mixture. The ionisation of the ionisable gas with the atmospheric plasma has the advantage over thermal ionisation using a flame that no combustible gas such as for example oxyhydrogen or hydrogen and oxygen needs to be supplied in order to generate the flame. Thus, air may be used as the working gas for producing the atmospheric plasma. As a rule, this is available as ambient air. Further, the environment of the plasma jet is heated by the plasma jet to a lesser degree than the environment of a flame, in particular an oxyhydrogen flame, is heated by the flame itself.

An electrical variable is understood to be any conceivable electrical variable, in particular a voltage, a current, the electric field or the resonance frequency of a resonance circuit.

In a preferred embodiment of the method, the electrical variable is measured between two electrodes, with a voltage being applied between the electrodes. In this way, the measurement of the electrical variable is realised in a very simple manner. Thus, for example the current flowing between the electrodes, the voltage or the capacitance of the electrode arrangement may be measured. The capacitance is influenced by the charged particles present between the electrodes. Further, the electrodes may be integrated as capacitance in a resonance circuit and the resonance frequency of the latter can be measured.

A further embodiment of the method is achieved by applying a voltage between 50 V and 350 V, in particular between 50 V and 250 V, preferably between 75 V and 150 V, between the electrodes. It has been shown that the method may be carried out particularly well at voltages within these voltage ranges. If the voltage is too high, there is a risk that the current flowing between the electrodes is too strong, so that the apparatus used for determining the current strength might be damaged. If the voltage is too low, the electric current flowing between the electrodes is very weak, so that the measurement of the current strength may have greater relative errors. Further, if the voltage is too low, the ions and electrons may be influenced to a large degree by the space-charge region occurring between the electrodes during ionisation.

In this method, either a DC voltage or an AC voltage can be applied between the electrodes. In the case of a DC voltage, the electrons and ions released during ionisation will always move towards the same electrode. In this way, a continuous measurement of the current flowing between the electrodes becomes possible. The application of an AC voltage has the advantage that the current strength measurement signal can be modulated via the AC voltage. This allows the measurement signal to be isolated from interferences by means of lock-in amplification. Also a square-wave voltage may be applied between the electrodes in order to discretise the measurements in time.

In a further embodiment of the method, a less noisy measurement is achieved owing to the fact that the plasma jet is substantially potential-free. As a result, no additional electric field is introduced into the area of ionisation by the plasma jet, by which the free electrons and ions might be influenced.

In a further preferred embodiment of the method, the plasma jet is produced by an arc discharge generated using a high-frequency high voltage. A high-frequency high voltage is typically to be understood to mean a voltage in the range of 1 to 50 kV, in particular 1 to 15 kV, at a frequency of 1 to 100 kHz, in particular 10 to 100 kHz, preferably 10 to 50 kHz. A plasma jet thus produced has a particularly low temperature at a high reactivity, so that the environment of the plasma jet is only slightly heated by the plasma jet.

In a further preferred embodiment, any influence on the gas mixture by the detection method is reduced by using an inert working gas, preferably nitrogen or an noble gas such as for example argon or helium, for generating the plasma jet. In this way, the gas mixture is not contaminated by any non-inert working gases. This is advantageous in particular if the method is used for analysing gas streams, wherein the gas stream is used further after the analysis, for example in a subsequent process step. This offers in particular also advantages over the flames used in the prior art, since the gas stream is not contaminated by any incompletely combusted gases, for example hydrogen, or by the combustion products generated, for example water or carbon dioxide.

In a further embodiment of the method, the gas mixture is derived from a process gas stream or an exhaust gas stream. In the case of a process gas stream, it is important to know the components contained in the gas mixture because they influence the composition, the character and the quality of the products produced by the process. Also in the case of an exhaust gas stream, for example from a combustion process, it is important to control the organic components contained therein, for example in order to comply with the legally stipulated emission limit values. It is therefore advantageous to cause the gas mixture from an exhaust gas stream to interact with the plasma jet, in order to determine in this way the concentration of the ionisable gas in the exhaust gas stream.

In a further preferred embodiment of the method, the gas mixture is generated by applying the plasma jet onto a contaminated surface. In this way, the plasma jet fulfils two functions at the same time. The plasma jet releases any contaminants from the surface and these contaminants are then ionised as a gas in the plasma jet. The measured electric current will then be a measure of the contamination removed from the surface. The application of the plasma jet onto the surface can then be carried out for example until the concentration of the ionisable gas has fallen below a certain level. In this way it is ensured that a certain degree of purity is achieved when cleaning the surface.

In the case of a conductive surface, for example a metallic one, this surface can replace one of the electrodes. In this case, the voltage is applied between the remaining electrode and the surface.

Alternatively, the remaining electrode may also be dispensed with by applying the voltage between the surface and the plasma nozzle.

In a further embodiment of the method, an analysis that deviates from the analysis of the gas mixtures as so far described, which is based on an electrical variable, is carried out by analysing the light generated in the interaction region of the plasma jet with the gas mixture and by determining the intensity of the light in at least one spectral range as a measure of the concentration of at least one substance in the gas mixture.

In the area of the plasma, substances of the gas mixture, in particular individual molecules and atoms, are excited by the energy contained in the plasma and emit light. Since these substances have a characteristic wavelength dependent emission behaviour, the concentration of the substance in the plasma can be readily determined by way of a wavelength selective analysis of the light emitted from the plasma. The concentration of an individual substance can be determined here via the intensity of the emitted light in a spectral range that includes a characteristic emission wavelength of the substance.

Preferably, optical emission spectroscopy (OES), which is a widely used technology, is used for determining the spectra. In this spectroscopy, a light beam is spectrally decomposed using a diffraction grating and is subsequently recorded by means of a line camera or a CCD camera. The spectra determined in this way show an intensity distribution as a function of the wavelength, so that a wavelength selective analysis of the light obtained from the plasma will become possible. Of course, also other spectroscopes can be used.

In a preferred manner it is further possible to determine the concentration of a substance in two different ways at the same time, which means both by means of an electrical variable and via the spectral light yield. In this way, accuracy may be enhanced. Alternatively, also a measurement signal for calibrating the other signal may be used. Further, it is possible to determine the concentration of substances that are not or not completely ionised in the plasma jet by analysing the light.

The analysis of the light is particularly advantageous when applying the plasma jet onto a contaminated surface.

The object that forms the basis of the invention is further achieved by means of an apparatus having the features further described herein.

The advantage of providing a plasma nozzle for generating an atmospheric plasma jet as a means for ionising ionisable gases lies in the fact that no combustible gas, in particular hydrogen and/or oxygen, needs to be provided in order to operate the plasma nozzle. Air that can be taken for example from the environment of the apparatus may be used as the working gas for generating the atmospheric plasma jet. Thus, the apparatus may be used in places where the supply of a combustible gas or the supply of a working gas other than air is not possible, is complex or dangerous. The gas inlet may be disposed in such a way that the gas mixture is introduced into the plasma jet before the plasma nozzle. It is also possible to provide a tubular extension of the outlet area of the plasma nozzle, into which the gas mixture is introduced.

A gas inlet is therefore understood to mean, for example, a feed line for the gas mixture. Alternatively, however, the apparatus may also be arranged in an environment containing a gas mixture, for example a gas stream, in such a way that the gas mixture to be analysed reaches the apparatus as a result of pressure, diffusion, lift or in a similar way. The gas inlet is then formed by at least one open side of the apparatus, into which a flow may be directed. Therefore, the term gas inlet is to be understood in a very broad sense.

In a preferred embodiment of the apparatus, a voltage between 50 V and 350 V, in particular between 50 V and 250 V, preferably between 75 V and 150 V can be generated using the voltage source. It has been shown that a voltage within these voltage ranges, which is applied between the electrodes, is particularly well suited for the operation of the apparatus.

A DC voltage source or an AC voltage source may be provided in the apparatus as the voltage source. A DC voltage source allows a continuous detection of the concentration of the ionisable gas, an AC voltage source can be used to suppress any disturbances.

A particularly compact and thus space-saving apparatus is achieved by arranging the plasma nozzle between the two electrodes. By means of this arrangement, a recombination of the electrons and ions released during ionisation of the gas is prevented since the differently charged particles flow immediately in opposite directions to the electrode that is correspondingly oppositely charged. The gas inlet is preferably located here in such a way that the gas mixture is directed into the plasma jet from a direction that is not parallel, preferably substantially vertical to the plane fixed by the direction of the plasma jet and the direction of a connection line between the two electrodes.

In a further preferred embodiment of the apparatus, the plasma nozzle is arranged in the area of the cathode. A cathode is here understood to mean the positively charged electrode. In this way, due to their lower the more mobile electrons are immediately sucked off, so that the risk of recombination with the ions is further reduced.

A further preferred embodiment of the apparatus is achieved by arranging the plasma nozzle between the gas inlet and the cathode. The anode is located on the side of the cathode that faces away from the plasma nozzle. The cathode preferably has an opening through which the ions can get into the area between the cathode and the anode. In this embodiment, the plasma jet is thus located outside of the space between the cathode and the anode. Thus, the electric field between the cathode and the anode is not influenced by the plasma jet.

A particularly low temperature of the plasma jet and consequently a low degree of heating of the environment of the plasma jet is achieved in a further embodiment of the apparatus in that the plasma nozzle has at least two electrodes and a voltage source for generating a high-frequency high voltage, said voltage source being connected to the at least two electrodes.

The method and the apparatus for detecting ionisable gases may be used in an exhaust gas purification system. If such a system includes means for removing ionisable molecules, in particular organic molecules, preferably hydrocarbons, and an apparatus for detecting ionisable gases, with said means for removing ionisable molecules and the gas inlet of the apparatus being arranged in the area of an exhaust gas line, then these means for removing ionisable molecules may be controlled via the value of the concentration of ionisable gases as determined by the apparatus by means of additional control means. In an analogous way, the method and the apparatus may also be used in a process with at least one process gas stream for controlling and/or adjusting the process gas composition.

By means of the apparatus, the concentration of ionisable gases in the exhaust gas mixture is detected. The means for removing these gases may be controlled via the detected concentration in such a way that the concentration falls below a certain limit value. Thus, such an exhaust gas purification system can be used to control the concentration of the ionisable gases and, for example, to comply with stipulated emission limit values. This is necessary because as a rule, a complete removal with the means for removing ionisable molecules is not possible.

In a preferred embodiment, the apparatus according to the invention is installed upstream or downstream of the means for removing ionisable molecules. In the case of an upstream arrangement, the concentration of the ionisable gases is determined prior to their removal, so that the means can be adjusted to the concentrations without delay. This is particularly advantageous in the case of rapidly fluctuating concentrations. In a downstream arrangement, the concentration of the ionisable gases is measured after the removal thereof, i.e. the end concentration is measured. As a result, it is simpler to control the means so as to achieve certain limit values. As a rule, a removal of the ionisable molecules is not to be understood to mean a complete removal.

BRIEF DESCRIPTION OF THE DRAWINGS

Further features and advantages of the present invention will be explained in more detail in the description of five exemplary embodiments with reference to the attached drawings, wherein.

DETAILED DESCRIPTION OF THE INVENTION

Figure 1:
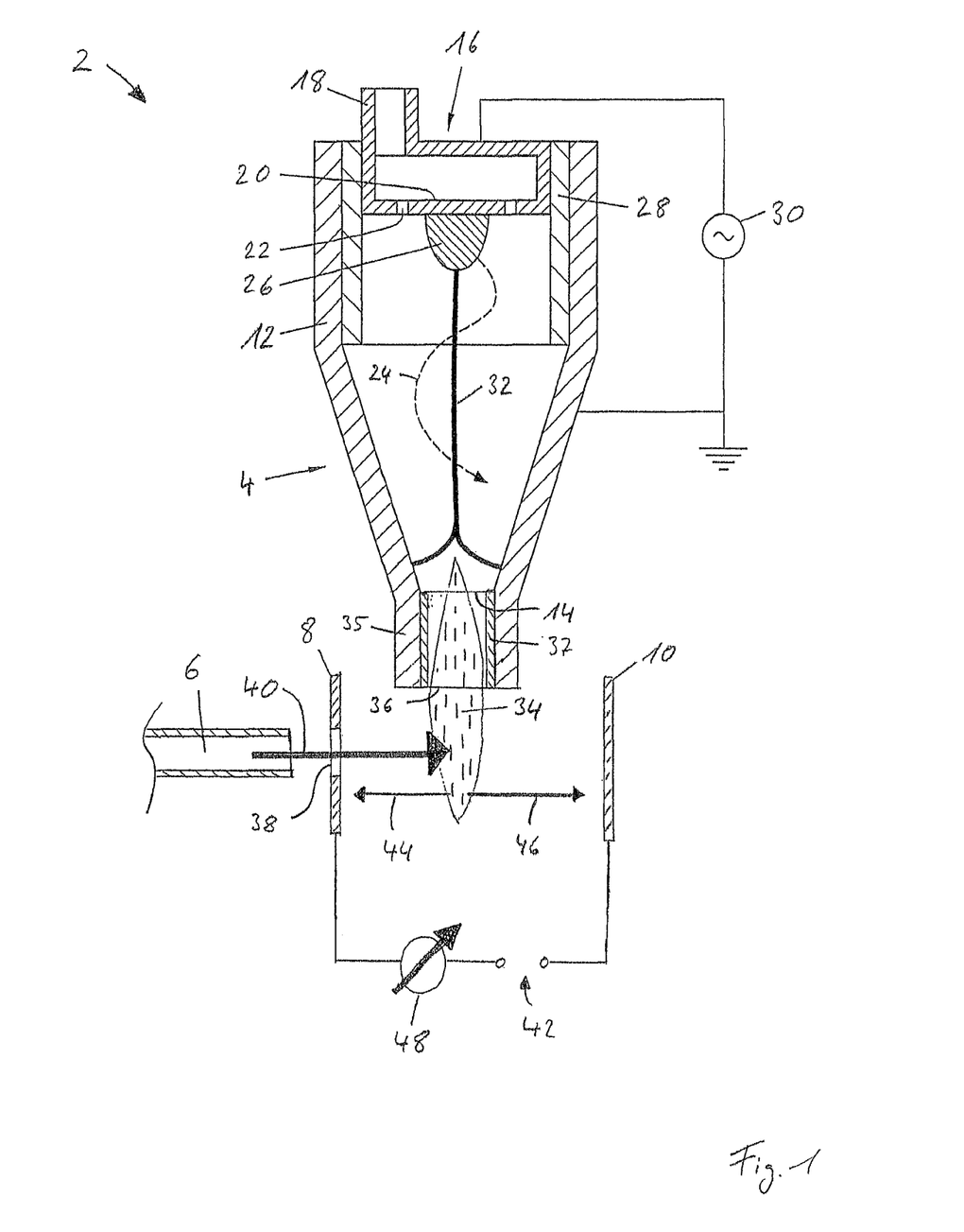
FIG. 1 shows a first exemplary embodiment of the apparatus according to the invention as well as a first exemplary embodiment of the method according to the invention.

FIG. 1 shows a first exemplary embodiment of the apparatus according to the invention as well as a first exemplary embodiment of the method according to the invention. The apparatus 2 comprises a plasma nozzle 4, a gas inlet 6, a first electrode 8 and a second electrode 10. The first electrode 8 is disposed between the gas inlet 6 and the second electrode 10. The plasma nozzle 4 is disposed between the first electrode 8 and the second electrode 10.

The plasma nozzle 4 includes a nozzle tube 12 made from metal which conically tapers towards a nozzle tube outlet 14. At the end opposite to the nozzle tube outlet 14, the nozzle tube 12 includes a twist device 16 having an inlet 18 for a working gas, for example for nitrogen or air. An intermediate wall 20 of the twist device 16 includes a ring of bores 22 arranged at an angle in the circumferential direction, by which bores the working gas is twisted. Therefore, the working gas flows through the conically tapered downstream part of the nozzle tube in the shape of a vortex 24, the core of which extends along the longitudinal axis of the nozzle tube.

An electrode 26 is centrally arranged on the underside of the intermediate wall 20 and coaxially protrudes into the nozzle tube in the direction of the tapered section. The electrode 26 is electrically connected to the intermediate wall 20 and the remaining parts of the twist device 16. The twist device 16 is electrically isolated from the nozzle tube 12 by a ceramic tube 28. A high-frequency high voltage is applied to the electrode 26 via the twist device 16, which voltage is generated by a transformer 30. The inlet 18 is connected to a pressurised working gas source having a variable throughput via a hose (not shown). The nozzle tube 12 is grounded.

The applied voltage generates a high-frequency discharge in the form of an arc 32 between the electrode 26 and the nozzle tube 12. The nozzle tube 12 thus constitutes the second electrode. An arc discharge is understood here to be such an arc. The term "arc" or the term "arc discharge" as synonymously used in this document is used here as a phenomenological description of the discharge, since the discharge occurs in the form of an arc.

Due to the twisted flow of the working gas this arc, however, is channelled in the vortex core along the axis of the nozzle tube 12, so that it does not branch out to the wall of the nozzle tube 12 until it reaches the area of the nozzle tube outlet 14. The working gas that rotates with a high flow speed in the area of the vortex core and thus in the immediate vicinity of the arc 32, comes into intimate contact with the arc and is therefore partially transferred into the plasma state, so that an atmospheric plasma jet 34 exits through the nozzle tube outlet 14, through the outlet area 35 and through the outlet opening 36 from the plasma nozzle 4. Therefore, the outlet area 35 may optionally include an isolating ceramic tube 37.

Alternatively, also a controlled DC voltage source may be provided instead of the transformer 30. This preferably includes a current controller or a current limiter. On account of the applied DC voltage, a brief discharge in the form of a spark or a permanent discharge in the form of an arc is then generated between the electrode 26 and the nozzle tube 12.

The first electrode 8 has an opening 38. A gas mixture 40 entering through the gas inlet 6 flows through this opening 38 into the area between the first electrode 8 and the second electrode 10. The gas mixture 40 interacts there with the plasma jet 34. As a result, the molecules of the ionisable gas are split into ions and electrons. In the case of hydrocarbons, for example $CHO^+$ ions are generated.

A voltage source 42 applies a voltage of for example 100 V between the first electrode 8 and the second electrode 10. This voltage source 42 may be a DC voltage source, with the first electrode 8 being connected to the positive pole. The first electrode 8 thus constitutes the cathode. The second electrode 10 connected to the negative pole correspondingly constitutes the anode. Alternatively, the voltage source 42 may also be an AC voltage source. As a result of the electric field between the first electrode 8 and the second electrode 10, the free electrons 44 are then attracted by the first electrode 8 and the positively charged ions 46 by the second electrode 10. The electric current flowing through is measured by a current measurement device 48 connected in series to the voltage source 42. The measured current value is a measure of the concentration of the ionisable gas in the gas mixture 40.

Figure 2:
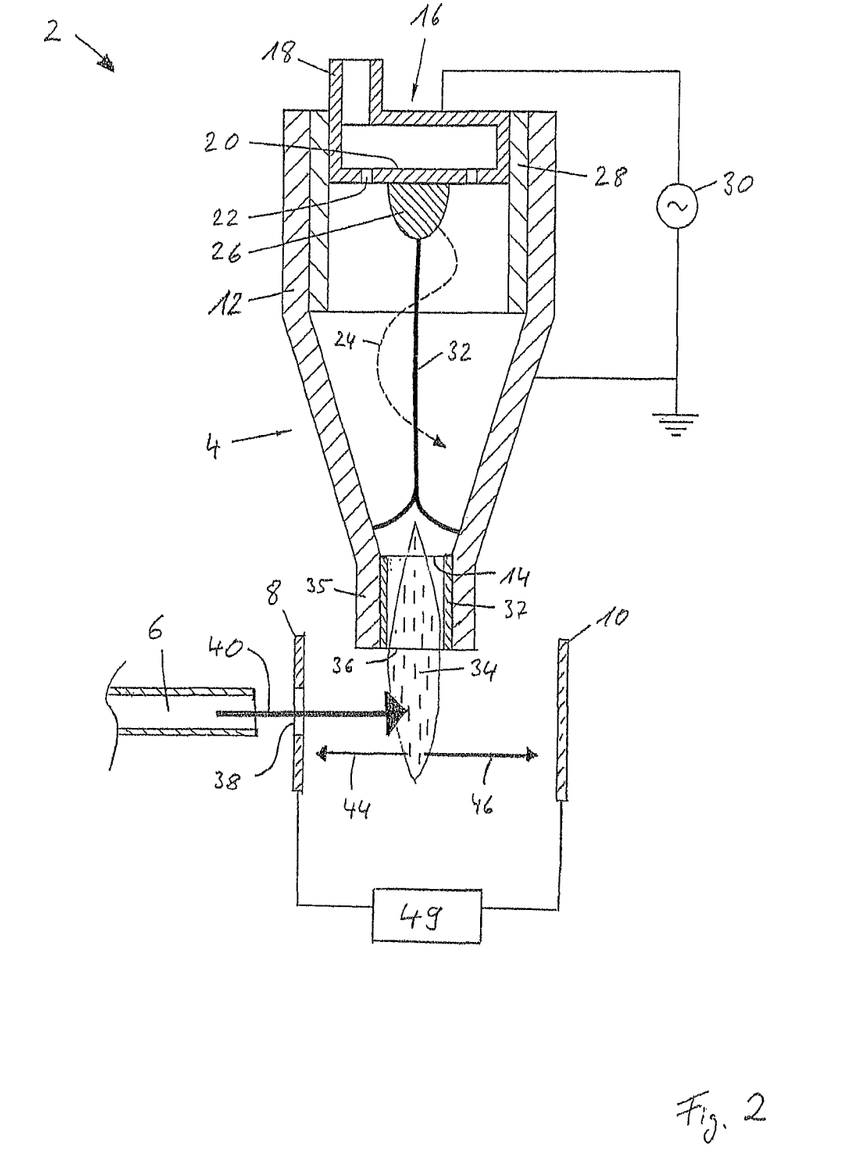
FIG. 2 shows a second exemplary embodiment of the apparatus according to the invention as well as a second exemplary embodiment of the method according to the invention.

FIG. 2 shows a second exemplary embodiment of the apparatus according to the invention and a second exemplary embodiment of the method according to the invention. This exemplary embodiment differs from the previous one in that a module 49 is connected between the first electrode 8 and the second electrode 10. The module 49 forms here, together with the electrodes 8, 10, an electric resonance circuit. For example, the module 49 includes a resistor and an inductance. The electrode arrangement of the electrodes 8, 10 essentially constitutes a capacitance. Also an additional capacitance may be provided in the module 49. The module 49 may further include a voltage source by which the resonance circuit may be excited. Further, means are provided in the module in order to determine the resonance frequency of the resonance circuit. As a result of the ions 46 or the electrons 44, the capacitance of the electrode arrangement and thus the resonance frequency of the resonance circuit change. This is therefore a measure of the ions 46 or the electrons 44.

Figure 3:
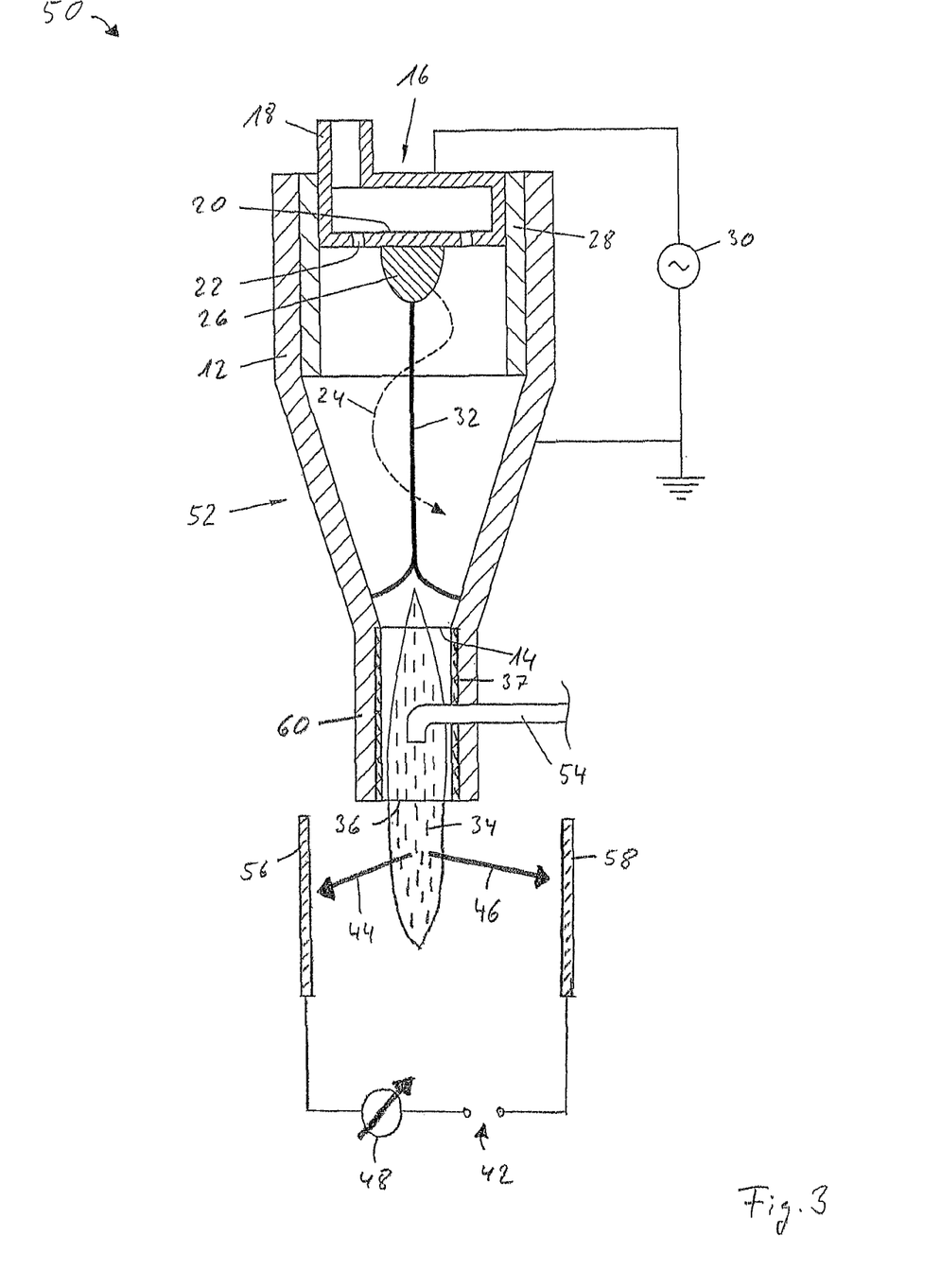
FIG. 3 shows a third exemplary embodiment of the apparatus according to the invention as well as a third exemplary embodiment of the method according to the invention.

FIG. 3 shows a third exemplary embodiment of the apparatus according to the invention and a third exemplary embodiment of the method according to the invention. The apparatus 50 comprises a plasma nozzle 52, a gas inlet 54, a first electrode 56 and a second electrode 58. The plasma nozzle 52 differs from the plasma nozzle 4 shown in FIG. 1 in that the plasma nozzle 52 has an extended outlet region 60. The gas inlet 54 is located in the outlet region 60, so that the gas mixture flowing in through the gas inlet 54 will reach the plasma jet 34 whilst still in the outlet region 60.

The ionisable gas contained in the gas mixture is ionised in the plasma jet 34. As soon as the ionised gas reaches the area between the first electrode 56 and the second electrode 58, the free electrons 44 generated during ionisation move towards the first electrode 56 and the positively charged ions 46 move towards the second electrode 58. By introducing the gas mixture into the outlet region 60 any non-ionised part of the ionisable gas is prevented from reaching the area between the two electrodes and from influencing there, for example, the free electrons 44 or the ions 46.

Of course, also a module as in the second exemplary embodiment may be arranged between the electrodes 56, 58 as an alternative to the voltage source 42 shown and the current measurement device 38.

Figure 4:
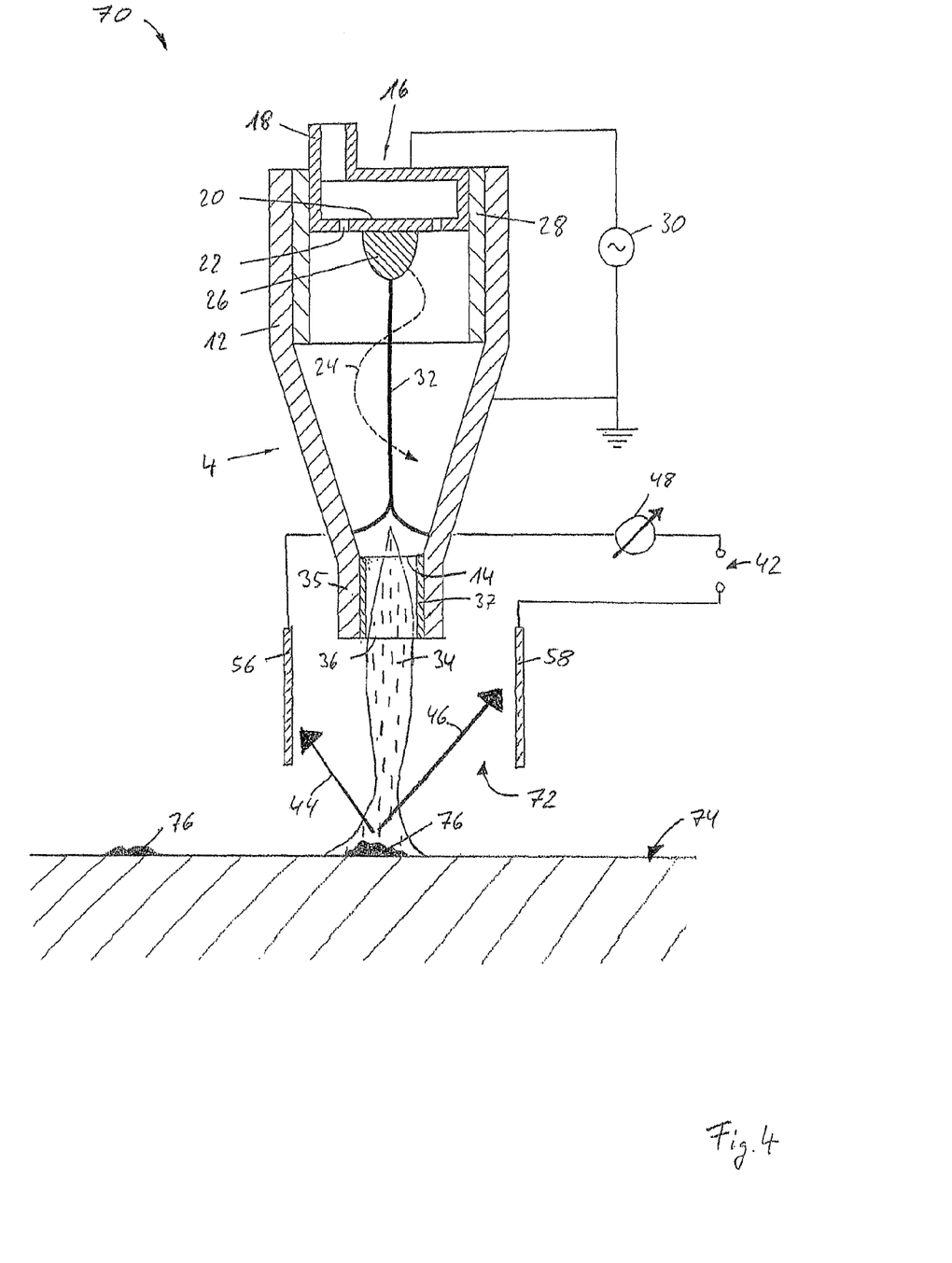
FIG. 4 shows a fourth exemplary embodiment of the apparatus according to the invention as well as a fourth exemplary embodiment of the method according to the invention.

FIG. 4 shows a fourth exemplary embodiment of the apparatus according to the invention and a fourth exemplary embodiment of the method according to the invention. The apparatus 70 includes a plasma nozzle 4 as shown in FIG. 1, a first electrode 56 and a second electrode 58. In the apparatus 70, the gas inlet is formed as a bottom opening 72 between the two electrodes. The apparatus 70 is positioned above a surface 74 that has contaminations 76. These contaminations may for example be organic contaminations, in particular hydrocarbons.

The plasma jet 34 exiting from the plasma nozzle 4 extends through the area between the two electrodes and impinges onto the surface 74. As a result of the energy provided in the plasma jet 34, the contamination 76 is gradually released from the surface 74. The ionisable molecules released from the surface 74 will then mix with the ambient gas to form a gas mixture which reaches the apparatus 70 through the bottom opening 72. The molecules are ionised in the plasma jet 34. The free electrons 44 generated thereby move towards the first electrode 56 and the positively charged ions 46 move towards the second electrode 58.

The plasma jet 34 may be applied to the surface 74 for example until the electric current measured by the current measurement device 48 falls below a specified value. In this way it is achieved that the application of the plasma jet onto the surface 74 will not cease until a certain part of the contamination 76 has been removed.

Figure 5:
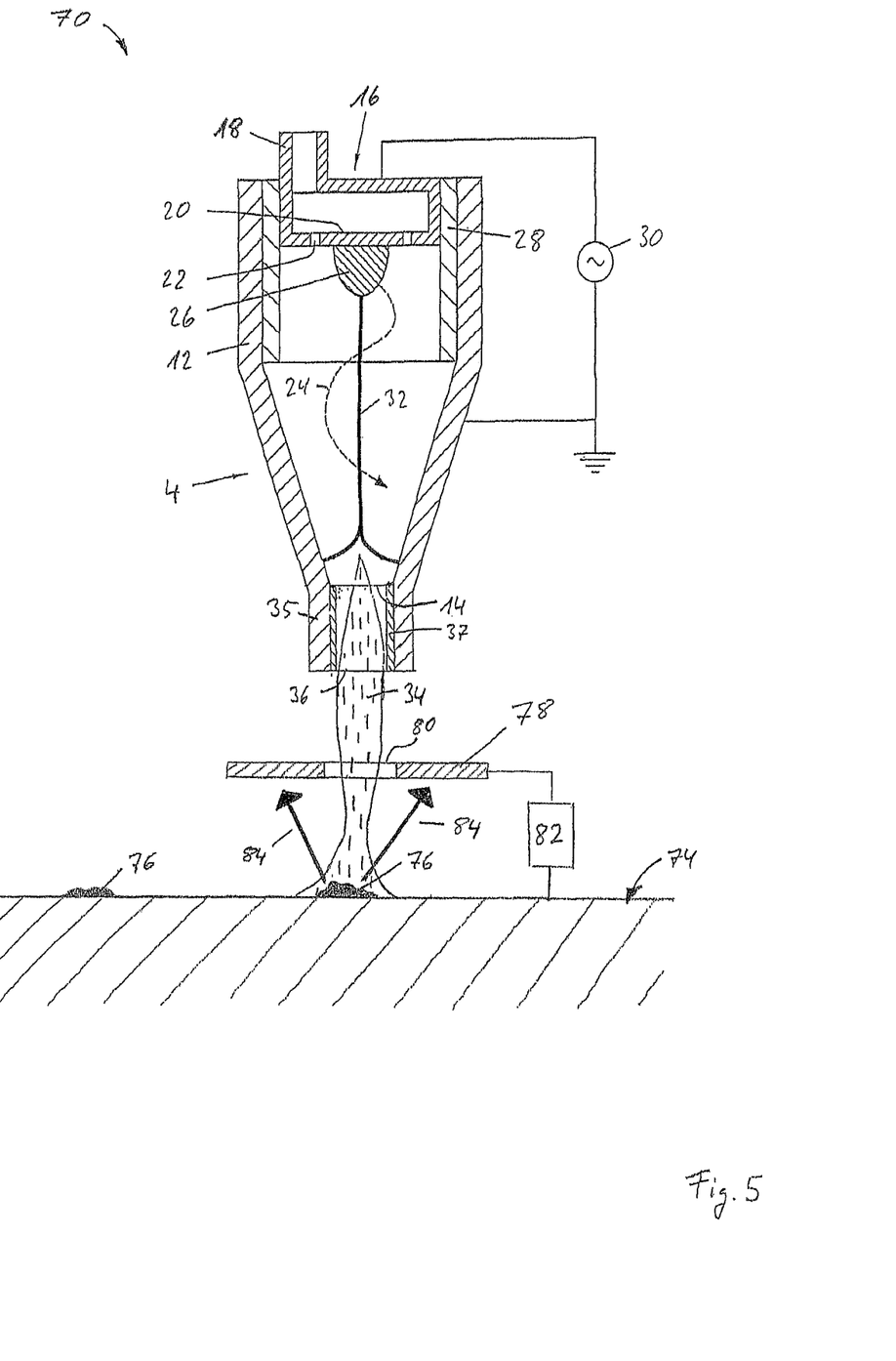
FIG. 5 shows a fifth exemplary embodiment of the apparatus according to the invention as well as a fifth exemplary embodiment of the method according to the invention.

FIG. 5 shows a fifth exemplary embodiment of the apparatus according to the invention and a fifth exemplary embodiment of the method according to the invention. This exemplary embodiment differs from the fourth exemplary embodiment in that an electrode 78 with an opening 80 is provided, through which the plasma jet 34 flows. Further, a module 82 is electrically connected to the electrode 78 and to the surface 74. The surface 74 thus constitutes the second electrode. The surface is therefore preferably electrically conductive. The module 82 can include for example a voltage source and a voltage measurement device. Alternatively, the module 82 may form a resonance circuit with the electrode arrangement of the electrode 78 and the surface 74. If a voltage that is negative relative to the surface 74 is applied to the electrode 78, the ions 84 generated during ionisation by the plasma jet 34 are moved towards the electrode 74. The electrons (not shown) flow off over the surface 74. In the case of the opposite polarity, the opposite correspondingly applies.

Figure 6:
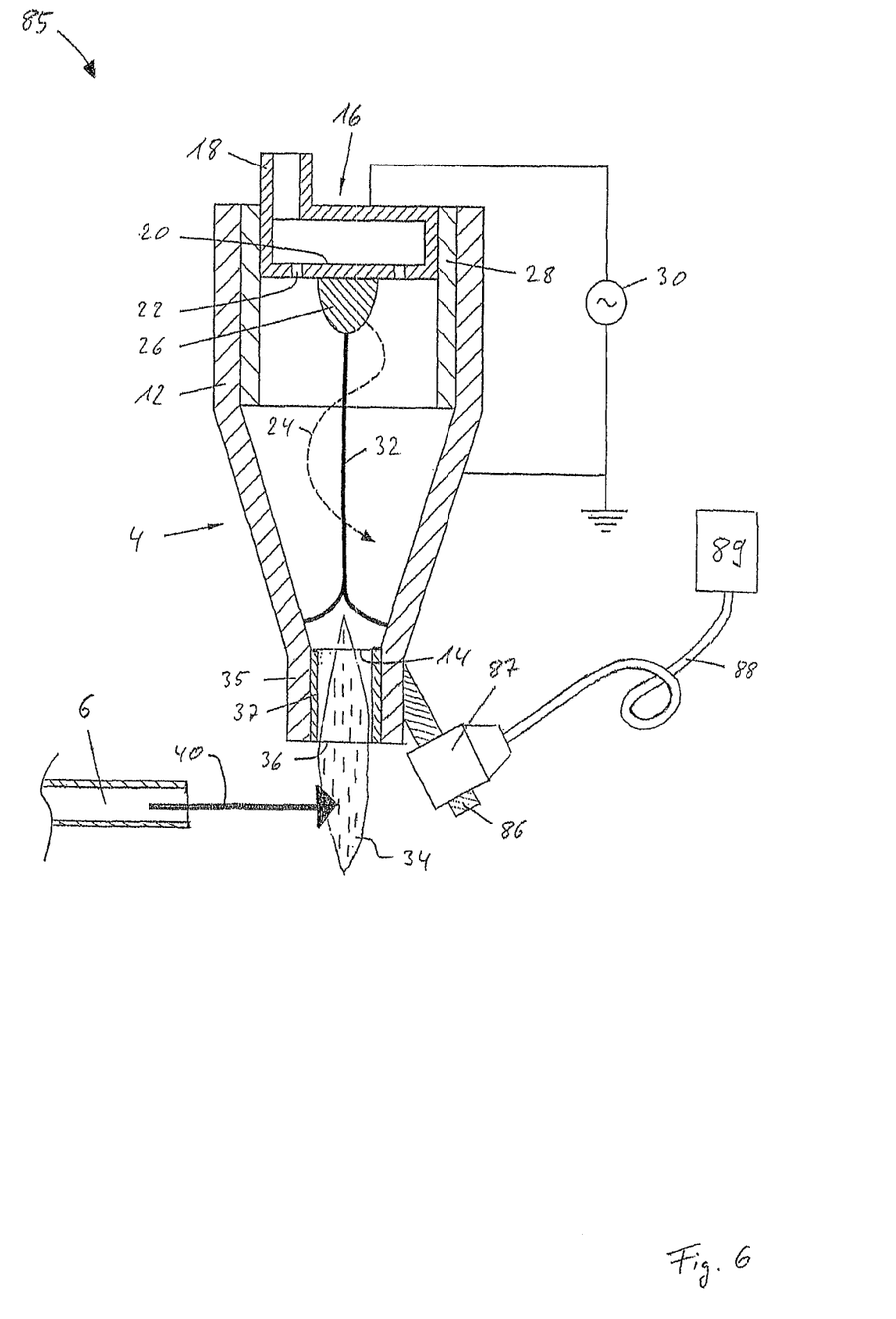
FIG. 6 shows an exemplary embodiment of an apparatus for a spectroscopic gas analysis.

FIG. 6 shows an exemplary embodiment of an apparatus for spectroscopic gas analysis. The plasma nozzle 85 differs from the plasma nozzle 2 shown in FIG. 1 in that, in addition, optical detection means 87 fixed to a bracket 86 are provided, which detection means are orientated towards the area in which the gas mixture 40 is made to interact with the plasma jet 34. The light emitted by the excited substances from this area is at least partially detected by the detection means 87 and is directed to a spectrometer 89 via a light conductor 88. In the spectrometer 89, the intensity is then measured in at least one spectral range, and by means of this measured value, the concentration of at least one substance in the gas mixture 40 is determined. In order to improve the detection of light, the detection means 87 may optionally include collection optics. The spectrometer 89 is preferably formed as a spectrometer for optical emission spectroscopy. Also an energy-dispersive detector may be used as the detection means 87, so that a separate spectrometer may be dispensed with. The detection means 87 may further be arranged to be separate from the plasma nozzle 85.

Of course it is possible to combine the features of the previous exemplary embodiments with each other. Thus, the gas mixture 40 ionised or excited by the plasma jet 34 may for example advantageously be analysed at the same time via provided electrodes as shown in FIGS. 1 to 5 and spectroscopically as shown in FIG. 6.

Figure 7:
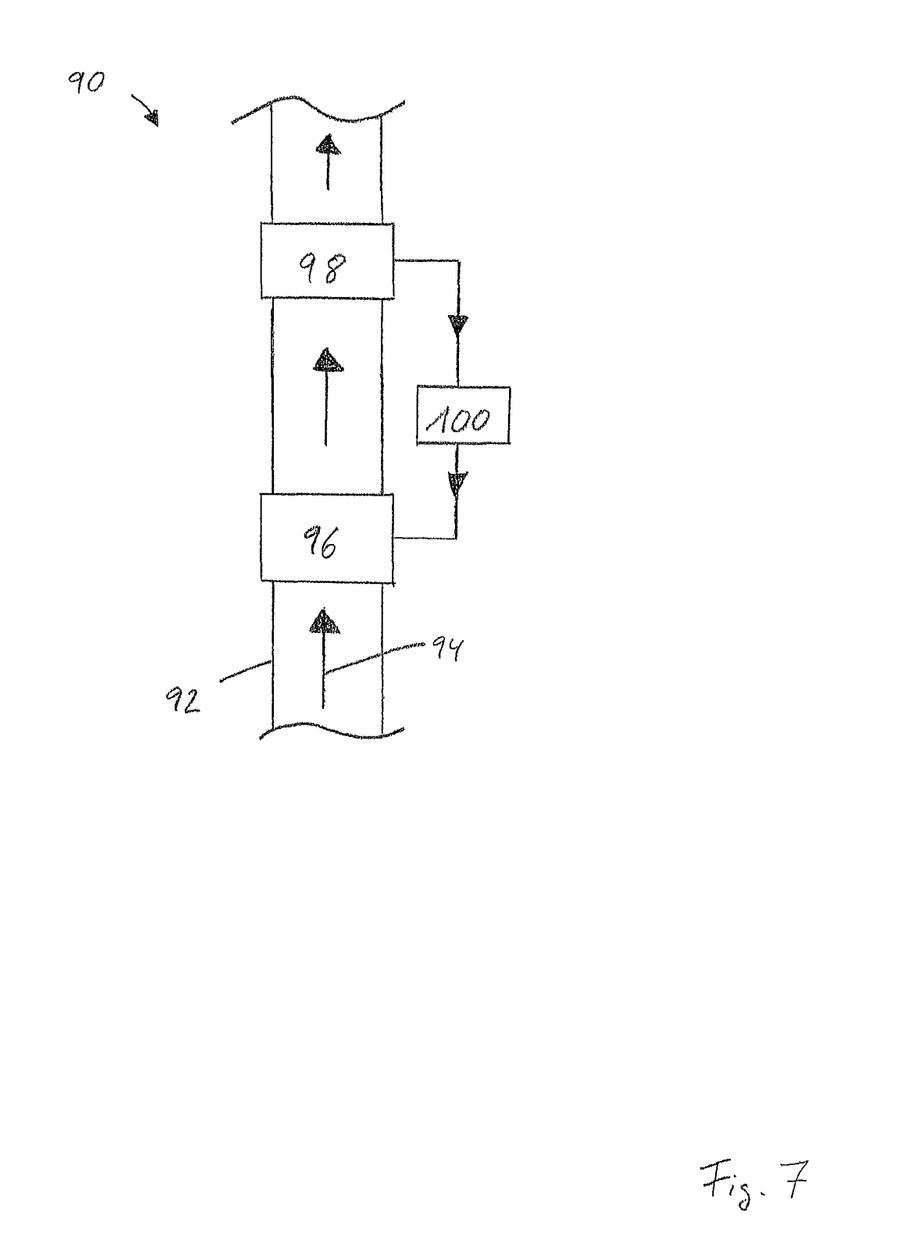
FIG. 7 shows a diagram of an exemplary embodiment of an exhaust gas purification system.

FIG. 7 shows a diagram of an exemplary embodiment of an exhaust gas purification system. The exhaust gas purification system 90 has an exhaust gas duct 92 that carries an exhaust gas 94. The exhaust gas 94 may for example be an exhaust gas mix from a combustion process, which contains an ionisable gas. The exhaust gas 94 first reaches the means 96 for removing ionisable molecules. The means 96 may for example be an adjustable catalyst. From there, the exhaust gas 94 flows to an apparatus 98 according to the invention for detecting ionisable gases, where the concentration of the ionisable gas in the exhaust gas 94 is detected.

The detected concentration of the ionisable gas is fed into a control unit 100 which generates a control signal for controlling the means 96. The control unit is designed here in such a way that the removal efficiency of the means 96 is enhanced in case the apparatus 98 detects an excessively high concentration of the ionisable gas. This ensures that after flowing through the exhaust gas purification device 90, the concentration of the ionisable gas in the exhaust gas 94 will be below a specified limit value.

Alternatively, it is also possible to arrange the apparatus 98 upstream of the means 96.

Instead of an exhaust gas purification device, the diagram shown in FIG. 6 may also be related to a process gas stream. Here, a process gas duct is provided instead of the exhaust gas duct 92 and a process gas instead of the exhaust gas 94. The concentration of the ionisable molecules in the process gas can then be controlled in an analogous manner using the means 96, the apparatus 98 and the controller 100. In this way, the controlled process gas stream can be fed to the next process step.

The invention claimed is:

1. A method for controlling an exhaust gas purification system, said method comprising the steps of:
    deriving a gas mixture from an exhaust gas stream;
    generating an atmospheric plasma jet exiting from a plasma nozzle;
    interacting the gas mixture containing an ionisable gas with the atmospheric plasma jet;
    at least partially ionizing the ionisable gas by the plasma jet thereby forming movable charge carriers, wherein the steps of interacting the gas mixture containing the ionisable gas with the atmospheric plasma jet and of at least partially ionizing the ionisable gas by the plasma jet thereby forming movable charge carriers are contemporaneous;
    measuring an electric current generated by the charge carriers so as to be used as a measure for the concentration of the ionisable gas in the gas mixture; and
    controlling the exhaust gas purification system to purify the exhaust gas via the determined value of the concentration of the ionisable gas.

2. The method according to claim 1, wherein the electric current is measured between two electrodes, with a voltage being applied between the electrodes.

3. The method according to claim 2, wherein the voltage applied between the electrodes is between 50 V and 350 V.

4. The method according to claim 2, wherein a DC voltage or an AC voltage is applied between the electrodes.

5. The method according to claim 1, wherein the plasma jet is substantially potential-free.

6. The method according to claim 1, wherein the plasma jet is produced by an arc discharge generated using a high-frequency high voltage.

7. The method according to claim 1, wherein for generating the atmospheric plasma jet, an inert working gas is used.

8. The method according to claim 1, wherein controlling the exhaust gas purification system comprises controlling a closed-loop catalytic converter for removing ionisable molecules.

\* \* \* \* \*